United States Patent [19]
Jacobson et al.

[11] Patent Number: 5,453,426
[45] Date of Patent: Sep. 26, 1995

[54] SULFUR-CONTAINING XANTHINE DERIVATIVES AS ADENOSINE ANTAGONISTS

[75] Inventors: Kenneth A. Jacobson, Silver Spring, Md.; Wolfgang Pfleidover, Konstanz, Germany; John W. Daly, Washington, D.C.; John L. Neumeyer, Wayland, Mass.

[73] Assignee: The United States of America as represented by the Department of Health and Human Services, Washington, D.C.

[21] Appl. No.: 359,959

[22] Filed: Dec. 20, 1994

Related U.S. Application Data

[63] Continuation of Ser. No. 73,654, Jun. 7, 1993, abandoned, which is a continuation of Ser. No. 340,351, Apr. 19, 1989, abandoned.

[51] Int. Cl.$^6$ .......................... C07D 473/06; A61K 31/52
[52] U.S. Cl. .......................... 514/263; 544/267; 544/268
[58] Field of Search ........................ 544/267, 268; 514/263, 262

[56] References Cited

U.S. PATENT DOCUMENTS

| | | | |
|---|---|---|---|
| 4,546,182 | 10/1985 | Kjellin et al. | 544/267 |
| 4,564,182 | 10/1985 | Kjellin et al. | 544/267 |
| 4,820,709 | 4/1989 | Hofer | 544/267 |
| 4,879,296 | 11/1989 | Daluge | 546/267 |
| 4,925,847 | 5/1990 | Hofer | 544/267 |

OTHER PUBLICATIONS

Chemical Abstracts vol. 111:77745(g) 1989.
Chemical Abstracts vol. 98 1252(z) (1983).
Chemical Abstracts vol. 98 125211z (1983).
Chemical Abstracts vol. 106 67009K (1987).

*Primary Examiner*—Nicholas Rizzo
*Attorney, Agent, or Firm*—Leydig, Voit & Mayer, Ltd.

[57] ABSTRACT

The present invention provides sulfur-containing xanthine derivatives which are 1,3-disubstituted with a $C_1$–$C_{12}$ alkyl, which may be further substituted with a hydroxy, amino, or halo group, and are 8-substituted with either a cycloalkyl, furyl, thienyl, or substituted phenyl group. These derivatives possess increased selectivity or potency at adenosine receptors.

26 Claims, No Drawings

SULFUR-CONTAINING XANTHINE DERIVATIVES AS ADENOSINE ANTAGONISTS

This is a continuation of application Ser. No. 08/073,654 filed on Jun. 7, 1993 now abandoned, which, in turn, is a continuation of application Ser. No. 07/340,351 filed on Apr. 19, 1989, now abandoned.

Sulfur-containing analogs of 8-substituted xanthines were prepared in an effort to increase selectivity or potency as antagonists at adenosine receptors. Either cyclopentyl- or various aryl-substituents were utilized at the 8-position, because of the association of these groups with high potency at $A_1$-adenosine receptors. Sulfur was incorporated on the purine ring at positions 2- and/or 6-, in the 8-position substituent in the form of 2- or 3-thienyl groups, or thienyl groups separated from an 8-aryl substituent through an amide-containing chain. The feasibility of using the thienyl group as a prosthetic group for selective iodination via its $Hg^{+2}$ derivative was explored. Receptor selectivity was determined in binding assays using

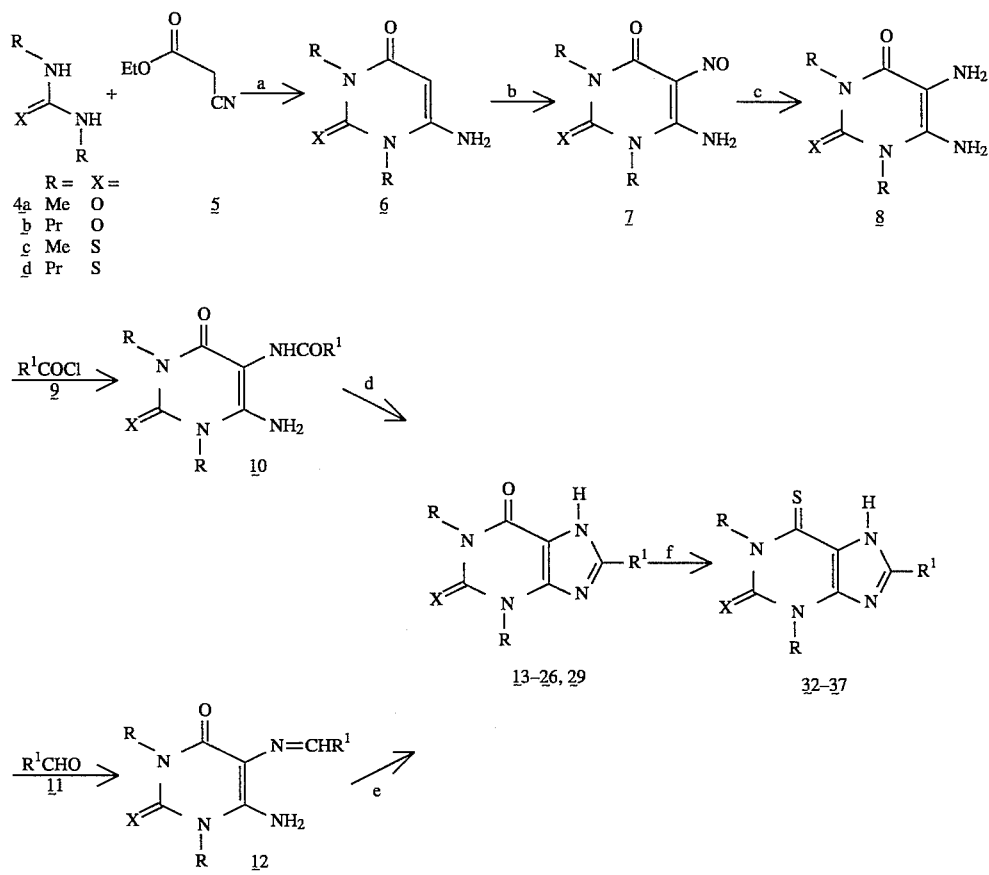

Scheme 1.

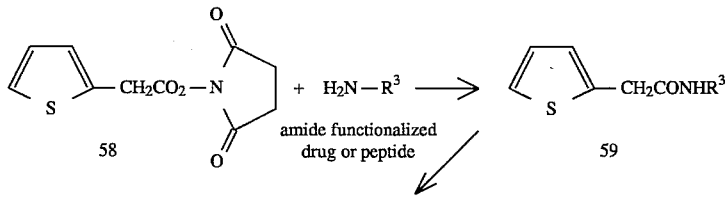

Scheme 2.
Use of 2-thienyl derivatives as prosthetic groups for mercuration and subsequent iodination (L = leaving group, such as N-hydroxysuccinimide).

Scheme 2.
Use of 2-thienyl derivatives as prosthetic groups for mercuration and subsequent iodination (L = leaving group, such as N-hydroxysuccinimide).

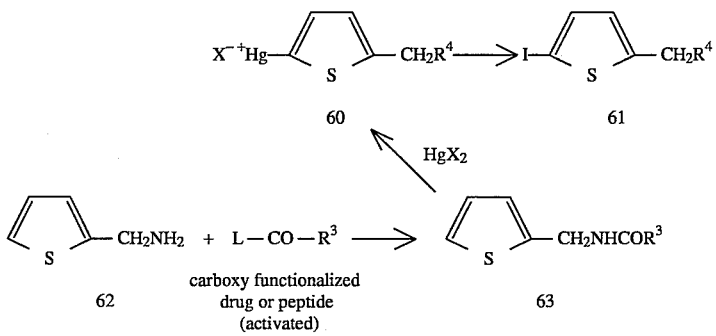

membrane homogenates from rat cortex ([$^3$H]N$^6$-phenylisopropyladenosine as radioligand) or striatum ([$^3$H]N-ethylcarboxamidoadenosine as radioligand) for $A_1$- and $A_2$-adenosine receptors, respectively. Generally 2-thio-8-cycloalkylxanthines were at least as $A_1$-selective as the corresponding oxygen analog. 2-Thio- 8-aryl derivatives tended to be more potent at $A_2$-receptors than the oxygen analog. 1,3-Dipropyl-8-(2-thienyl)-2-thioxanthine was >285-fold $A_1$-selective.

Compounds of the invention are of the general formula:

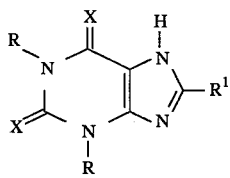

wherein X is O or S, with the proviso that at least one X is S; R is alkyl of 1–12 carbons which may be substituted with hydroxy, amino, halo, or an aryl, $R^1$ is hydrogen, cycloalkyl, furyl, thienyl, phenyl which may be substituted with a substituent $R^2$ which is COOH, COOAlkyl, CONH(CH$_2$)$_n$NHR$^3$, alkoxyamid, benxyloxyamid, alkylamino; $R^3$ is alkyl, alkylcarbonyl, alkoxyamidoalkyl. In all cases alkyl includes cyclic, branched, or straight chain and may be substituted with halo, alkoxy, hydroxy, amino, amido, or carboxy groups.

BACKGROUND OF THE INVENTION 1,3-Dialkyl- and other xanthine derivatives inhibit many of the pharmacological and physiological effects of adenosine, eg. the cardiac depressive,[1] hypotensive,[1] anti-diuretic,[2] and anti-lipolytic effects,[3] by acting as competitive antagonists at $A_1$ and $A_2$-adenosine receptor subtypes. The naturally-occurring caffeine and theophylline, 1, are the most widely used xanthine drugs. However, they are non-selective and relatively weak adenosine antagonists ($K_i$-values of 10 µM or greater). Synthetic analogs of theophylline, containing 1,3-dipropyl-, 8-aryl-, and 8-cycloalkyl-substitutions, are more potent as adenosine antagonists. [4-6] The combination of 1-, 3-, and 8-position substitutions has resulted in analogs such as CPX,[5,6] 2, and XAC,[7] 3, which are more than four orders of magnitude more potent than theophylline in binding at $A_1$-adenosine receptors, and $A_1$-selective by factors of 300 and 60, respectively.

Xanthines having thio-substitutions at the 2- and/or 6-position have been reported to act as antagonists as $A_2$-receptors in human fibroblasts[21] and as phosphodiesterase inhibitors with potency comparable to or greater than theophylline.[8,9a] Remarkably, 6-thiocaffeine and 6-thiotheophylline cause cardiac depression rather than stimulation.[9b] Recently, 6-thiocaffeine and 6-thiotheophylline were reported to induce tracheal relaxation, without cardiac or behavioral stimulation.[9a] Thio-substitution of the NH at position 7 of 8-phenyltheophylline reduced activity by 1000-fold at an $A_1$ receptor and by nearly 100-fold at an $A_2$ receptor.[20]

DESCRIPTION OF THE INVENTION

The compositions of the invention provide means of increasingly selective acitivity as adenosine receptor antagonists in xanthine drugs.

Various 8-substituted xanthine and thioxanthine derivatives were synthesized via 1,3-dialkyl-5,6-diaminouracils as shown in Scheme 1. The substituted uracil and 2-thiouracil intermediates were prepared via an optimized Traube synthesis.[6,7a] 1,3-Dimethyl- and 1,3-di-n-propyl-5,6-diaminouracil and their 2-thio derivatives were obtained by condensation of the corresponding dialkyl urea, 4a and b, or thiourea, 4c and d, with ethyl cyanoacetate, 5. The products after ring closure, substituted 6-aminouracil derivatives, 6, were then nitrosated at the 5-position. The nitroso group was reduced through chemical reduction or catalytic hydrogenation to form the intermediate 1,3-dialkyl-5,6-diaminouracil derivatives, 8, in good yield.

The next step of the synthesis was to form the imidazole ring of the purine nucleus resulting in the xanthine derivatives, as listed in Table 1 (compounds 1,2, 13–28). The more nucleophilic 5-amino group of compound 8 was acylated using a carboxylic acid chloride, 9, forming the 1,3-dialkyl-5-acylamino- 6-aminouracil derivatives, 10. 1,3-Dialkyl-5-acylamino-6-aminouracils derived from thiophene-2-carboxylic acid and -3-carboxylic acid chlorides and from cyclopentane carboxylic acid chloride were isolated and characterized (Table 2). The various 1,3-dialkyl-5-acylamino-6-aminouracil derivatives were then cyclized to the corresponding xanthine and 2-thioxanthine derivatives (Table 3) by treatment with aqueous sodium hydroxide.

For 8-(p-carboxymethyloxyphenyl)xanthine derivatives related to a xanthine amine congener, compound 3, an alternate route was used to form the imidazole ring. 1,3-Dipropyl-5,6-diaminouracil, 8b, or corresponding 2-thiouracil, 8d, was condensed with p-formylphenyloxyacetic acid, forming the imine, 12. Upon oxidation, the carboxylic acid congeners 27 (XCC) and 28 were obtained. The xanthine carboxylic acid derivatives were then esterified giving the ethyl esters, 29 and 30, respectively, which were treated with neat ethylene diamine as previously reported[7] to give the amine derivatives 3 and 31. Since the $A_2$- potency of compound 31 was enhanced over the oxygen analog (see below), compound 3, we synthesized other 8-aryl-2-thioxanthine derivatives in an effort to increase $A_2$-potency. Other amine derivatives were synthesized through aminolysis reactions (compounds 32–35) or by carbodiimide coupling (compounds 36–39) as reported.[10b] Lysyl conjugates 38–43 were prepared as described.[10c]

An N-hydroxysuccinimide ester derivative, 44, was reported to be an irreversible inhibitor of $A_1$-adenosine receptors at concentrations greater than 50 nM.[10a] If shown to be potent and non-selective adenosine antagonist this xanthine may be a potential inhibitor of both $A_1$ and $A_2$-adenosine receptors. Certain isothiocyanate-containing xanthines related to compound 3 also have been shown to be chemically reactive with $A_1$-receptors. [10a] Efforts to synthesize analogous xanthineisothiocyanates containing the 2-thio substitution were unsuccessful, likely due to side reactions involving the more reactive thio group.

A thiation reaction was used to generate 6-thioxanthine derivatives from the corresponding oxygen analogs. It is known[11] that xanthine derivatives are preferentially thiated at the 6-position using $P_4S_{10}$. Dioxane was the favored reaction medium to give high yields of the anticipated 6-thio- and 2,6-dithioxanthines (compounds 52–57). For example, CPX was converted to 8-cyclopentyl-1,3-dipropyl-6-thioxanthine, 55, using this thiation reaction.

Iodinated xanthine derivatives, synthesized using a prosthetic group[12] or by classical methodology, have been introduced as high affinity radioligands for adenosine receptors.[12,13] We have explored the use of a 2-thienyl substituent as a site for selective iodination, via mercuration (Scheme 2). These substituted thiophene derivatives such as 59 and 63 undergo regioselective mono-mercuration at the unsubstituted 2-position, rapidly and at ambient temperature, in the presence of stoichiometric quantities of mercury salts such as mercuric acetate.[14] The 2-mercurothiophene salt, 60, is then exposed to elemental iodine resulting in the corresponding 2-iodothiophene derivative, 61.

New prosthetic groups designed for facile radiodination of functionalized drugs and peptides are still being sought.[15,16] We have used thiophene-2-acetic acid (as its reactive N-hydroxysuccinimide ester, 58, and thiophene-2-methylamine, 62, as prosthetic groups for iodination, via mercuration.

Compound 58 reacted with XAC, 3, to form an amide, compound 46. This 2-thienyl xanthine was readily mercurated to give 47.

Iodination via 2-mercurothiophene intermediates as in Scheme 2 may be carried out selectively in the presence of other susceptible aromatic groups, such as phenols. Compound 58 reacted with L-tyrosyl-glycine to form an amide (compound 59, in which $R^3$=CH(CH$_2$φOH)CONHCH$_2$COOH). Upon sequential treatment with mercuric acetate and iodine (1 equiv.), the corresponding monoiodinated peptide derivative, 61 ($R^4$= CONHCH(CH$_2$φOH)CONHCH$_2$COOH), was obtained in high yield.

The N-succinoyl derivative (63a, $R^3$=(CH$_2$)$_2$COOH) of thiophene-2-methylamine was mercurated to form an internal salt, 60b ($R^4$=NHCO(CH$_2$)$_2$COOH) which precipitated from methanol. Upon treatment with iodine an immediate reaction occurred. This reaction was followed by NMR in $d_6$-DMSO. The complete reaction of the 2-mercurothiophene derivative was indicated by shifts of the thiophene aromatic signals to 6.68 and 7.13 ppm from TMS, corresponding to the 2-iodo derivative, 61b.

Results—Pharmacology

Affinity at $A_1$- and $A_2$-adenosine receptors was measured in competitive binding assays, using as radioligands [$^3$H]N$^6$-phenylisopropyladenosine [17] (with rat cerebral cortical membranes) and [$^3$H]5'-N-ethylcarboxamidoadenosine (with rat striatal membranes), [18] respectively.

A sulfur substitution at the 2-position carbonyl group of 1,3-dialkylxanthines usually did not decrease the affinity of the xanthines for $A_1$ or $A_2$ adenosine receptors. In the case of the 2-thio analog of CPX, compound 14, the $A_1$ affinity was enhanced by the thio substitution. The 2-thio xanthine amine congener, compound 30, bound with greater affinity at $A_2$-receptors and with less affinity at $A_1$-receptors than the corresponding oxygen analog, compound 3. Potency at $A_2$-receptors was enhanced 7-fold by the 2-thio substitution in the case of a carboxylic acid congener (compounds 27 and 28).

N-Methylated analogs (32–37) of compound 31 were prepared. As in the 2-oxo series, the secondary N-methylamine derivative, 33, was the most potent at $A_2$-receptors with a $K_i$-value of 6.8 nM. Thus, the combination of two modifications of compound 3 have enhanced its $A_2$ affinity 10-fold.

A sulfur substitution at the 6-position carbonyl group of 1,3-dialkylxanthines was not well tolerated at either $A_1$ or $A_2$ binding sites. Thus, the 6-thio analog of CPX, 55, was 17-fold less potent than CPX at $A_1$-receptors. The 6-thio analog of 1,3-diethyl- 8-phenylxanthine, 57, was 23-fold less potent than DPX, 24, at $A_1$-receptors and 12-fold less potent at $A_2$-receptors. 2,6-Dithio analogs, such as 53, were intermediate in potency between the corresponding 2-thio and 6-thio analogs.

Substitutions of thienyl and furyl groups at the 8-position of xanthines have approximately equivalent effects on affinity at both receptor subtypes. Both substitutions are generally slightly less potent than the corresponding 8-phenylxanthine analogs. For both thienyl and furyl derivatives (several of which were reported previously, by Bruns et al[18]), attachment at the 3-position relative to the heteroatom (sulfur or oxygen, respectively) results in greater potency at adenosine receptors than attachment at the 2-position. Preference for 3-thienyl derivatives was evident particularly at the $A_2$-subtype (cf. 18 vs. 17 and 20 vs. 19).

1,3-Dipropyl-8-(2-thienyl)-2-thioxanthine, 22, did not bind measurably to $A_2$-receptors at its limit of solubility (approximately 10 μM), at which concentration there was not even a partial displacement of tritiated [$^3$H]N-ethylcarboxamidoadenosine from striatal membranes. Thus, compound 22 is >285-fold $A_1$-selective in these binding assays.

2-Thio analogs of caffeine were also prepared. 8-Cycloalkyl- 2-thio analogs (eg. cyclohexyl and cyclopentyl) of 1,3,7-trialkylxanthines are A2 selective adenosine antagonists. When 8-aryl substituents are present, the caffeine analogs tend to be more non-selective than the corresponding 8-cycloalkyl derivative.

The following compounds were prepared as caffeine analogs:
Compound 64 8-Cyclopentyl-2-thiocaffeine
65 8-(2-Thienyl)-2-thiocaffeine
66 8-(2-Thienyl)caffeine Discussion We have found that 2-thioxanthines are very similar in potency to the corresponding oxygen analogs. In certain cases, as for the CPX analog, 14, and an 8-(2-thienyl) derivative, 22, a greater margin of $A_1$-selectivity may be achieved using the 2-thio substitution. A 6-thio substitution is not well tolerated at either $A_1$ or $A_2$ receptors.

The feasibility of using a 2-thienyl moiety as a prosthetic group for selective iodination via its $Hg^{+2}$ derivative was explored. By facile and selective mercuration at the 2-thienyl Ar—H, a site for rapid and regioselective (in the presence of phenols) iodination is created. A xanthine conjugate of XAC and 2-thienylacetic acid was sequentially mercurated and iodinated by this scheme, resulting in an iodinated xanthine with potential use as an antagonist radioligand for adenosine receptors. This scheme may have applicability to other receptor ligands, including tyrosyl peptides, in which iodination in the presence of essential phenolic groups, is desired.

Experimental Section

XAC (8-(2-aminoethylaminocarbonylmethyloxyphenyl-1,3-dipropylxanthine), 2-chloroadenosine, and 8-cyclohexyl-1,3-dipropylxanthine were obtained from Research Biochemicals, Inc. (Natick, Mass.). Compounds 32, 34, 36, 38, 42, 50, and 51 were reported previously.[7c,10b] Amino acid derivatives of XAC and the 2-thio analog were synthesized in the manner previously described,[7c] using the water soluble 1-(3-dimethylaminopropyl)- 3-ethylcarbodiimide hydrochloride (EDAC) in dimethylformamide. p-Formylphenyloxyacetic acid was obtained from Eastman-Kodak (Rochester, N.Y.). [$^3$H]N$^6$-phenylisopropyladenosine and [$^3$H]5'-N-ethylcarboxamidoadenosine were from Dupont NEN Products, Boston, Mass. Thiophene-2-acetic acid was from Aldrich.

New compounds were characterized by 300 MHz proton NMR (unless noted chemical shifts are in $d_6$-DMSO in ppm from TMS), chemical ionization mass spectroscopy (CIMS, $NH_3$, Finnigan 1015 spectrometer), and C, H, and N analysis. UV spectra were measured in methanol, and the results are expressed as peak wavelengths in nm with log ε values in parentheses.

General procedure for compound 10

A 1,3-disubstituted 5,6-diaminouracil or the corresponding 1-thiouracil (10 mmol) was suspended in 10 ml of absolute pyridine and then under stirring 11 mmol of the acid chloride (freshly prepared) was added dropwise. After 5 h stirring at room temperature the reaction mixture was poured slowly into 100 ml of $H_2O$, and the precipitate was collected by suction filtration. Purification was done by recrystallization from a EtOH/$H_2O$-mixture. Yields ranged from 70 to 90%.

General procedure for compounds 13–26

A 1,3-disubstituted 5-acylamino-6-aminouracil or the corresponding 2-thiouracil (10 mmol) was heated under reflux in a mixture of 40 ml of 1N NaOH and 10 ml of EtOH for 1 h. The hot solution was acidified with acetic acid resulting in the formation of a precipitate upon cooling. The precipitate was collected and recrystallized from a $H_2O$/EtOH-mixture. Yield 80–90% of colorless crystals. $^1$H-NMR spectrum of compound 13: δ 3.86 (3H, s, $CH_3$), 3.68 (3H, s, $CH_3$), 3.19 (m, 1H, cyclohex C1), 2.0 (m, 2H, cyclohex C2 and C5), 1.6–1.8 (m, 6H, cyclohex). The NMR spectra of the other compounds were consistent with the assigned structures.

(8-[2-Dimethylaminoethyl[N-methylamino[carbonyl[methyl[ oxyphenyl]]]]]-2-thio-1,3-dipropylxanthine), 37

Compound 28, 8-(4-(carboxymethyloxy)phenyl)-1,3-dipropyl-2-thioxanthine (21 mg, 52 μmol), N,N,N'-trimethylethylenediamine (Aldrich, 20 mg, 0.20 mmol), EDAC (45 mg, 0.23 mmol), and N-hydroxybenzotriazole (25 mg, 0.18 mmol) were combined in 1 mL DMF. After stirring overnight, 0.5 mL of sodium carbonate (pH 10, 0.5M) and 2 mL of saturated NaCl were added. After cooling overnight a white precipitate was collected. Yield 13 mg (52%). The NMR and mass spectra were consistent with the assigned structure.

N-Succinimidyl 8-[2-[4-(6-Carboxy-n-hexyl)carbonylaminoethyl[amino[carbonyl[methyloxyphenyl]]]]]-1,3-dipropyl-2-thioxanthine, 45

Compound 31 (10.4 mg, 0.024 mmol) was added to a solution of disuccinimidyl suberate (13.1 mg, 0.036 mmol, Pierce, Rockford, Ill.) in DMF (1 mL) and vigorously stirred for 2 h or until complete by TLC (CHCl3/MeOH/AcOH, 18/1/1). Dry ether (2 mL) was then added to the suspension followed by the addition of petroleum ether until cloudy. The suspension was allowed to stand at 0° C. for 1 h then filtered to give an off-white powder. Yield 11.5 mg, (68%). Mp 160°–168° C. $^1$H-NMR (DMSO-d6) 0.90 (t, J=7.2 Hz, 3 H) 0.94 (t, J=7.2 Hz, 3 H), 1.28 (br m, 4 H), 1.44 (m, 2 H), 1.71 (m, 2 H), 1.83 (m 2 H), 1.83 (t, J=7.6 Hz, 2 H), 2.65 (t, J= 7.0 Hz, 2 H), 2.79 (s, 4 H), 3.15 (br s, 4 H), 3.32 (s, $H_2O$), 4.45 (br t, J=7.2 Hz, 2 H), 4.54 (s, 2 H), 4.59 (br t, J=7.2 Hz, 2 H), 7.10 (d, J=8.7 Hz, 2 H), 7.83 (br s, 1 H), 8.11 (d, J= 8.7 Hz 2 H), 8.18 (br s, 1 H).

General procedure for thiation reaction

The appropriate xanthine or 2-thioxanthine derivative (10 mmol) was heated with 6 g of $P_4S_{10}$ in 100 ml of dioxane for 3–5 h under reflux. Insoluble material was removed by filtration, and the filtrate was added dropwise to 200 ml of $H_2O$ with stirring. The precipitate was collected and purified by recrystallization from a $H_2O$/EtOH-mixture. Yield 80–85%.

N-Succinimidyl thiophene-2-acetic acid, 58

Thiophene-2-acetic acid (1.61 g, 11 mmol), dicyclohexylcarbodiimide (2.34 g, 11 mmol), and N-hydroxysuccinimide (1.30 g, 11 mmol) were added to 50 mL of ethyl acetate containg 10% DMF. After stirring for two hours, the urea was removed by filtration. The filtrate was washed with aqueous acid/base and evaporated. The residue was recrystallized from ethyl acetate/petroleum ether. Yield 2.01 g (74%).

5-Mercurothiophene-2-acetate, 60a ($R^4$=—COO$^-$), mercuration reaction

Thiophene-2-acetic acid (0.39 g, 2.8 mmol) was dissolved in 8 mL methanol. Mercuric acetate was added with stirring, and a white precipitate appeared shortly thereafter. After one hour, 4 mL ether was added and the solid was collected by filtration. Yield of 60a 0.88 g (93%). Mass spectrum (CI-$NH_3$) shows a peak at 360 z/e corresponding to m+1+$NH_3$.

The thiophene-xanthine derivative, 46, was prepared as reported previously. Upon mercuration in dimethylformamide by a method, a solid product, compound 46, was obtained and characterized by californium plasma desorption mass spectoscopy.

2-(N-Succinoylaminomethyl)-5-mercurothiophene, 60b (R=NHCO($CH_2$)$_2$COO$^-$)

Compound 63a (60.5 mg, 0.28 mmol) was dissolved in 5 mL methanol and treated with 100 mg (0.31 mmol) mercuric acetate. First a solution formed, followed by crystallization of product. After one hour, ether was added, and the precipitate was collected. Yield 98 mg (84%), m.p. 230° C. dec.

This compound was converted to the corresponding 5-iodo derivative upon treatment at room temperature with iodine or iodine monochloride. H-NMR of 2-(N-succinoylaminomethyl)-5-mercurothiophene, 61b: 8.46 (1H, t, NH), 7.13 (1H, d, Ar-4), 6.68 (1H, d, Ar-3), 4.37 (2H, d, $CH_2N$), 2.43 (2H, $CH_2$), 2.35 (2H, $CH_2$).

5-Iodothiophene-2-acetic acid, 61a ($R^4$=—COOH)

Compound 60a (75 mg, 0.22 mmol) was suspended in 5 mL of dimethylformamide containing 5% DMSO. Iodine crystals (77 mg, 0.31 mmol) was added with stirring. A solution formed within one minute. 1M Hydrochloric acid was added and the mixture was extracted three times with ethyl acetate. The combined organic layers were dried ($Na_2SO_4$) and evaporated. The product was purified by column chromatography on silica gel. $R_f$ of product (silica, ethyl acetate/petroleum ether) was 0.79.

The identical product was obtained as follows: N-Iodosuccinimide (236.2 mg, 1.05 mmol) was added to a stirred suspension of compound 59a (326.2 mg, 0.95 mmol) in methanol (30 mL). After 16 h the suspension was filtered and the methanol removed in vacuo. The remaing oil was redissolved in ethyl acetate, washed with 0.5N HCl and the product was extracted into a 0.5N NaOH solution. The basic fraction was washed with $CH_2Cl_2$, acidified to pH 1.0 with 1N HCl, and extracted with EtOAc. The product was chromatographed on a silica gel column (eluent, 17/2/1, $CHCl_3$/MeOH/AcOH), and the solvents removed from the product fractions in vacuo. Acetic acid was removed by azeotropic distillation with petroleum ether. The light yellow oil was redissolved in ethyl acetate, and ether was added forming a precipitate which was removed by filtration. Evaporation of the solvent gave compound 61a as a waxy yellow solid (110 mg, 43%).

Peptide derivatives of thiophene-2-acetic acid

Compound 58 reacted with L-tyrosyl-glycine (274 mg, 1.15 mmol) in dimethylformamide to give N-(thiophene-2-acetyl)-L-tyrosyl-glycine (230 mg, 55% yield). Upon mercuration in dimethylformamide as for compond 60a, N-(5-mercurothiophene-2-acetyl)-L-tyrosyl-glycine (40% yield) was obtained.

2-(N-Succinoylaminomethyl)-thiophene, 63a (R=$(CH_2)_2$COOH)

Thiophene-2-methylamine (Aldrich, 2.37 g, 21 mmol) was dissolved in 20 mL tetrahydrofuran and treated with a solution of succinic anhydride (2.1 g, 21 mmol) in 20 mL dimethylformamide. After one half hour, ethyl acetate (50 mL) was added, and the mixture was extracted with citric acid (1M) three times and with water. The organic layer was dried ($MgSO_4$). Solvent was removed and petroleum ether was added causing white crystal of 62a to precipitate. Yield 9.4%, mp 130° C. The NMR and mass spectra were consistent with the assigned structure. UV spectrum $1_{max}$ 233 nm (log ε 4.019).

Biochemical assays

Stock solutions of xanthines were prepared in the millimolar concentration range in dimethylsulfoxide and stored frozen. Solutions were warmed to 50° prior to dilution in aqueous medium. Inhibition of binding of 1 nM [$^3$H]$N^6$-phenylisopropyladenosine to $A_1$ adenosine receptors in rat cerebral cortical membranes was assayed as described.[17] Inhibition of binding by a range of concentrations of xanthines was assessed in triplicate in at least three separate experiments. $IC_{50}$ values computer-generated using a nonlinear regression formula on the Graphpad program, were converted to $K_i$ values using a $K_D$ value for [$^3$H]PIA of 1.0 nM and the Cheng-Prusoff equation.[19]

Inhibition of binding of [$^3$H]N-ethylcarboxamidoadenosine to $A_2$-adenosine receptors in rat striatal membranes was measured as described,[18] except that 5 mM theophylline was used to define non-specific binding. $N^6$-Cyclopentyladenosine was present at 50 nM to inhibit binding of the ligand at $A_1$-adenosine receptors. Inhibition of binding by a range of concentrations of xanthines was assessed in triplicate in at least three separate experiments. $IC_{50}$-values were converted to Ki-values by the method of Bruns et al,[18] using a conversion factor derived from the affinity of [$^3$H]N-ethylcarboxamidoadenosine at $A_2$ receptors and the Cheng-Prusoff equation.[19]

Acknowledgements: This project has been supported in part by the National Institutes of Health SBIR grant No.1 R34 AM 37728-01 to Research Biochemicals, Inc.

Abbreviations: XAC, xanthine amine congener, 8-(4-(2-amino-ethylaminocarbonylmethyloxy)phenyl)- 1,3-dipropylxanthine; CPX, 8-cyclopentyl-1,3-dipropylxanthine; EDAC, dimethylaminopropylethylcarbodiimide hydrochloride; HOBt, 1-hydroxybenzotriazole.

Pharmaceutical compositions may be prepared using the usual carriers and may be given by mouth, parenterally, or as compositions particularly adapted for uptake though the mucosa, such as cyclodextrin inclusion complexes and the like. Compositions particularly suited for oral dosing include elixirs and tablets. Dosage will depend on the size of the patient and the particular preparation given. An effective dosage of 0.1 to 10 mg/kg would be the usual dosage range.

References:
1. Fredholm, B. B.; Jacobson, K.; Jonzon, K.; Kirk, K.; Li, Y.; Daly, J. *J. Cardiovasc. Pharmacol.* 1987, 9, 396.
2. Collis, M. G.; Baxter, G. S.; Keddie, J. R. *J. Pharm. Pharmacol.* 1986, 38, 850.
3. Londos, C.; Wolff, T. *Proc. Natl. Acad. Sci. USA* 1977, 74, 5482.
4. Bruns, R. F.; Daly, J. W.; Snyder, S. H. *Proc. Natl. Acad. Sci. USA* 1983, 80, 2077.
5. Bruns, R. F.; Fergus, J. H.; Badger, E. W.; Bristol, J. A.; Santay, L. A.; Hays, S. J. *Naunyn-Schmiedeberg's Arch. Pharmacol.* 1987, 333, 64.
6. Shamim, M. T., Ukena, D.; Padgett, W. L.; Hong, O.; Daly, J. W. *J. Med. Chem.*, 1988, 31, 613.
7. a) Jacobson, K. A.; Kirk, K. L.; Padgett, W. L.; Daly, J. W. *J. Med. Chem.* 1985, 28, 1334; b) Jacobson, K. A.; Ukena, D.; Kirk, K. L.; Daly, J. W. *Proc. Natl. Acad. Sci. USA* 1986, 83, 4089; c) Jacobson, K. A.; Kirk, K. L.; Padgett, W.; Daly, J. W. *Mol. Pharmacol.*, 1986, 29, 126.
8. Wu, P. H.; Phillis, J. W.; Nye, M. J. *Life Sciences* 1982, 31, 2857.
9. a) Fassina, G.; Gaion, R. M.; Caparrotta, L.; Carpenedo, F. *Naunyn-Schmiedeberg's Arch. Pharmacol.* 1985, 330, 222. b) Ragazzi, E.; Froldi, G.; Santi Soncin, E.; Fassina, G. *Pharmacol. Res. Commun.* 1988, 20, 621.
10. a) Jacobson, K. A.; Barone, S.; Kammula, U.; Stiles, G. *J. Med. Chem.*, in press; b) K. A. Jacobson, R. de la Cruz, R. Schulick, L. Kiriasis, W. Padgett, W. Pfleiderer, K. L. Kirk, J. L. Neumeyer, and J. W. Daly, *Biochem. Pharmacol.* 1988, 37, 3653; c) Jacobson, K. A; Ukena, D; Padgett, W.; Daly, J. W; Kirk, K. L., *J. Med. Chem.* 1987, 30, 211.
11. Dietz, A. J.; Burgison, R. M. *J. Med. Chem.* 1966, 9, 500.
12. Stiles, G. L.; Jacobson, K. A. *Mol. Pharmacol.* 1987, 32, 184.
13. Linden, J.; Patel, A.; Earl, C. Q.; Craig, R. H.; Daluge, S. M. *J. Med. Chem.* 1988, 31, 745.
14. Spande, T. *J. Org. Chem.* 1980, 45, 3081.
15. Seevers, R. H.; Counsell, R. E. *Chem. Rev.* 1982, 82, 575.

16. Khawli, L. A.; Adelstein, S. J.; Kassis, A. I. Abstract ORGN80 at the 196th National Meeting of the Americal Chemical Society, Los Angeles, Calif., Sep. 25–30, 1988.
17. Schwabe, U.; Trost, T. *Naunyn-Schmiedeberg's Arch Pharmacol.* 1980, 313, 179.
18. Bruns, R. F.; Lu, G. H.; Pugsley, T. A. *Mol. Pharmacol.* 1986, 29, 331.
19. Cheng, Y. C.; Prusoff, W. H. *Biochem. Pharmacol.* 1973, 22, 3099.
20. Daly, J. W.; Hong, O.; Padgett, W. L.; Shamim, M. T.; Jacobson, K. A.; Ukena, D. *Biochem. Pharmacol.* 1988, 37, 655.
21. Bruns, R. F., Biochem. Pharmacol., 1981, 30, 325.

TABLE 1

Potencies of xanthine derivatives at adenosine $A_1$ and at $A_2$ receptors in nanomolar concentration units.[a,b]

| Compound | R | R$^1$ | X | $K_i$ $A_1$-receptors | $K_i$ $A_2$-receptors | $K_i(A_2)/K_i(A_1)$ |
|---|---|---|---|---|---|---|
| 1a | Me | H | O | 8,470 ± 1490[c] | 25,300 ± 2000[c] | 2.99 |
| 1b | Pr | H | O | 450 ± 25[c] | 5,160 ± 590 | 11.5 |
| 2a | Me | cyclopentyl | O | 10.9 ± 0.9[c] | 1,440 ± 70[c] | 133 |
| 2b | Pr | cyclopentyl | O | 0.9 ± 0.1 | 420 | 470 |
| 13 | Me | cyclopentyl | S | 8 | 1,390 ± 88 | 170 |
| 14 | Pr | cyclopentyl | S | 0.655 ± 0.058 | 314 ± 62 | 479 |
| 15 | Me | 2-furyl | O | 350 ± 20[c] | 2,780 ± 50[c] | 7.94 |
| 16 | Me | 3-furyl | O | 72.4 ± 3.7[c] | 984 ± 70[c] | 13.6 |
| 17 | Me | 2-thienyl | O | 233 ± 48.6 | 1,630 ± 179 | 6.97 |
| 18 | Me | 3-thienyl | O | 152 ± 27 | 841 ± 109 | 5.53 |
| 19 | Pr | 2-thienyl | O | 16.1 ± 1.96 | 381 ± 27.7 | 23.6 |
| 20 | Pr | 3-thienyl | O | 10.0 ± 0.03 | 121 ± 18.2 | 12.1 |
| 21 | Me | 2-thienyl | S | 221 ± 43.3 | 1,740 ± 153 | 7.87 |
| 22 | Pr | 2-thienyl | S | 35.1 ± 6.0 | >10,000 | >285 |
| 23 | Me | phenyl | O | 86.0 ± 2.8[c] | 848 ± 115[c] | 9.85 |
| 24 | Et | phenyl | O | 44.5 ± 1.2[c] | 836 ± 73[c] | 19.4 |
| 25 | Pr | phenyl | O | 10.2 ± 2.6[c] | 180 ± 29[c] | 17.8 |
| 26 | Me | phenyl | S | | | |
| | R$^2$ | | | | | |
| 27 | COOH | | O | 58 ± 3 | 2,200 ± 526 | 37.8 |
| 28 | COOH | | S | 53.8 ± 7.1 | 315 ± 60.8 | 5.86 |
| 29 | COOEt | | O | 42 ± 3 | >10,000 | >238 |
| 30 | COOEt | | S | 6.78 ± 0.64 | >5,000 | >740 |
| 3 | CONH(CH$_2$)$_2$NH$_2$ | | O | 1.2 ± 0.5 | 63 ± 21 | 52.5 |
| 31 | CONH(CH$_2$)$_2$NH$_2$ | | S | 2.69 ± 0.77 | 26.3 ± 1.76 | 9.8 |
| 32 | CONH(CH$_2$)$_2$NHCH$_3$ | | O | 15.1 ± 1.6[d] | [9.3 ± 2.1][f] | [0.62] |
| 33 | CONH(CH$_2$)$_2$NHCH$_3$ | | S | 2.4 ± 0.28 | 6.80 ± 1.36 | 2.8 |
| 34 | CONH(CH$_2$)$_2$N(CH$_3$)$_2$ | | O | 2.8 ± 0.19[d] | 5.03 ± 0.54 | 1.8 |
| 35 | CONH(CH$_2$)$_2$N(CH$_3$)$_2$ | | S | 2.55 ± 0.60 | 27.9 ± 7.5 | 11 |
| 36 | CONCH$_3$(CH$_2$)$_2$N(CH$_3$)$_2$ | | O | 0.93 ± 0.03[d] | 6.26 ± 0.25 | 6.7 |
| 37 | CONCH$_3$(CH$_2$)$_2$N(CH$_3$)$_2$ | | S | 2.57 ± 0.67 | 24.5 ± 8.4 | 9.5 |
| 38 | CONH(CH$_2$)$_2$NHCOCHNHCOOBu$^t$ (D), (CH$_2$)$_4$, C$_6$H$_5$CH$_2$OCONH | | O | 12 | e | e |
| 39 | CONH(CH$_2$)$_2$NHCOCHNHCOOBu$^t$ (D), (CH$_2$)$_4$, C$_6$H$_5$CH$_2$OCONH | | S | 84 | 870 | 10 |
| 40 | CONH(CH$_2$)$_2$NHCOCHNH$_2$ (D), CF$_3$COOH. (CH$_2$)$_4$, C$_6$H$_5$CH$_2$OCONH | | O | 6.4 ± 2.7 | 191 ± 13 | 30 |
| 41 | CONH(CH$_2$)$_2$NHCOCHNH$_2$ (D), CF$_3$COOH. (CH$_2$)$_4$, C$_6$H$_5$CH$_2$OCONH | | S | 8.9 | 322 ± 17 | 36 |
| 42 | CONH(CH$_2$)$_2$NHCOCHNH$_2$ (D), 2HBr. (CH$_2$)$_4$, NH$_2$ | | S | 0.87 ± 0.09 | 180 | 210 |

TABLE 1-continued

Potencies of xanthine derivatives at adenosine $A_1$ and at $A_2$ receptors in nanomolar concentration units.[a,b]

| Compound | | | X | $K_i$ $A_1$-receptors | $K_i$ $A_2$-receptors | $K_i(A_2)/K_i(A_1)$ |
|---|---|---|---|---|---|---|
| 43 | $CONH(CH_2)_2NHCOCHNH_2$ (D)<br>2HBr.  $(CH_2)_4$<br>       $NH_2$ | | S | 13.0 ± 3.5 | 46.8 ± 9.4 | 3.6 |
| 44 | $CONH(CH_2)_2NH-$<br>$CO(CH_2)_6COON$ | | O | 3.69 ± 0.71[d] | 207 ± 57[d] | 56 |
| 45 | $CONH(CH_2)_2NH-$<br>$CO(CH_2)_6COON$ | | S | 33.5 | e | e |
| 46 | $CONH(CH_2)_2NH-$<br>$-COCH-$ | | O | 18.3 ± 3.0 | 147 ± 5 | 8.1 |
| 47 | $CONH(CH_2)_2NH-$<br>$-COCH_2-$  $-HgOAc$ | | O | 16.2 ± 2.7 | 458 ± 34 | 28.3 |
| 48 | $CONH(CH_2)_2NH-$<br>$-COCH_2-$  $-I$ | | O | 11.3 ± 1.5 | 116 ± 25 | 10.3 |
| 49 | $CONH(CH_2)_2NH-$<br>$CO(CH_2)_6CONHCH_2-$ | | | 7.44 ± 0.98 | 630 ± 160 | 85 |
| 50 | $CONH(CH_2)_2NHCOCHNHCOO-Bu^f$<br>               $CH_2$   (L) | | O | 17.6 ± 1.6 | e | e |
| 51 | $CONH(CH_2)_2NHCOCHNH_2$ (L)<br>$CF_3COOH.$     $CH_2$ | | O | 1.3 ± 0.12 | e | e |
| | R | $R^1$ | | | | |
| 52 | Me | cyclopentyl | S | 40.5 ± 6.6 | 11,500 ± 628 | 285 |
| 53 | Pr | cyclopentyl | S | 4.87 ± 0.82 | 2,780 ± 730 | 572 |
| 54 | Me | cyclopentyl | O | 202 ± 26 | 8,980 ± 1300 | 44.4 |
| 55 | Pr | cyclopentyl | O | 15.5 ± 1.5 | 3,360 ± 270 | 217 |
| 56 | Me | phenyl | O | 1,380 ± 74 | 11,300 ± 777 | 8.18 |
| 57 | Et | phenyl | O | 1,010 ± 321 | 3,510 ± 290 | 3.47 |

[a] - $K_i$ value from a single determination run in triplicate or average of thre ± S.E.M.
[b] - Inhibition of binding of [$^3$H]-phenylisopropyladenosine to $A_1$-receptors i rat cortical membranes and binding of [$^3$H]N-ethylcarboxamidoadenosine to $A_2$ adenosine receptors in rat striatal membranes was measured as described.[18,19]
[d] - Values taken from Bruns et al.[18]
 - Values taken from Jacobson et al.[10]
[e] - Not determined.
[f] - $K_b$ for inhibition of N-ethylcarboxamidoadenosine-stimulated adenylat cyclase, pheochromocytoma PC12 cell membranes.[10b]

TABLE 2

Synthesis and characterization of 1,3-dialkyl-5-acylamino-6 aminouracils.

| Compound | R | $R^1$ | X | % Yield | Mp (°C.) | Formula | Analysis |
|---|---|---|---|---|---|---|---|
| 10a | Me | cyclopentyl | S | 71 | 253 | $C_{12}H_{18}N_4O_2S$ | C, H, N |
| 10b | Pr | cyclopentyl | S | 92 | 103 | $C_{16}H_{26}N_4O_2S \cdot H_2O$ | C, H, N |
| 10c | Me | 2-thienyl | O | 76 | >300 | $C_{11}H_{12}N_4O_3S$ | C, H, N |
| 10d | " | 3-thienyl | O | 78 | >300 | $C_{11}H_{12}N_4O_3S$ | C, H, N |
| 10e | Pr | 2-thienyl | O | 88 | 143 | $C_{15}H_{20}N_4O_3S$ | C, H, N |
| 10f | " | 3-thienyl | O | 88 | 144 | $C_{15}H_{20}N_4O_3S$ | H, N; C[a] |
| 10g | Me | 2-thienyl | S | 83 | >300 | $C_{11}H_{12}N_4O_2S_2$ | C, H, N |
| 10h | Pr | " | S | 80 | 150 | $C_{15}H_{20}N_4O_2S_2$ | C, H, N | a - Calculated 53.56% C; found 52.95%.

TABLE 3

Synthesis and characterization of xanthine derivatives.

| Compound | % Yield | Mp (°C.) | Formula | Analysis |
|---|---|---|---|---|
| 13 | 91 | 278 | $C_{12}H_{16}N_4OS$ | C, H, N |
| 14 | 89 | 217 | $C_{16}H_{24}N_4OS$ | C, H, N |
| 17 | 82 | >300 | $C_{11}H_{10}N_4O_2S$ | C, H, N |
| 18 | 92 | >300 | $C_{11}H_{10}N_4O_2S$ | C, H, N |
| 19 | 85 | 259 | $C_{15}H_{18}N_4O_2S$ | C, H, N |
| 20 | 87 | 267 | $C_{15}H_{18}N_4O_2S$ | C, H, N |
| 21 | 71 | >340 | $C_{11}H_{10}N_4O_2S_2$ | C, H, N |
| 22 | 92 | 298 | $C_{15}H_{18}N_4OS_2$ | C, H, N |
| 26 | — | 350 | $C_{13}H_{12}N_4OS$ | C, H, N |
| 33 | 95 | 206–208 | $C_{22}H_{30}N_6O_3S.1/4H_2O$ | C, H, N |
| 35 | 93 | 238–240 | $C_{23}H_{32}N_6O_3S.3/4H_2O$ | C, H, N |
| 37 | 52 | 172–174 | $C_{24}H_{34}N_6O_3S.1/2H_2O$ | C, H, N |
| 39 | 92 | 210–212 | $C_{40}H_{54}N_8O_8S$ | C, H, N |
| 41 | 84 | 182–187 | $C_{37}H_{47}F_3N_8O_8S.1/2CF_3COOH.1/2H_2O$ | C, H, N |
| 43 | 97 | 238–242d | $C_{27}H_{40}N_8O_4S.3HBr.3/2H_2O$ | C, H, N |
| 45 | 68 | 160–168 | $C_{33}H_{43}N_7O_8S$ | C, H; N[b] |
| 48 | 85 | 240d | $C_{27}H_{31}N_6O_5SI.2.5H_2O$ | C, H, N |
| 52 | 85 | 236 | $C_{12}H_{16}N_4S_2$ | C, H, N |
| 53 | 84 | 135 | $C_{16}H_{24}N_4S_2$ | — |
| 54 | 79 | 241 | $C_{12}H_{16}N_4OS$ | C, H, N |
| 55 | 81 | 153 | $C_{10}H_{24}N_4OS$ | C, H, N |
| 56 | 84 | 256 | $C_{13}H_{12}N_4OS$ | C, H, N |
| 57 | 72 | 223 | $C_{15}H_{16}N_4OS$ | H; C, N[a] |
| 60b | 84 | 230 | $C_{11}H_9NO_3SHg$ | C, H, N |
| 61a | 43 | 71–73 | $C_6H_5O_2SI.0.5H_2O$ | C, H | a - Calculated 59.32% C, 18.65% N; found 58.52% C, 18.12% N.
b - Calculated 14.05% N; found 15.42% N.

Supplementary information:

Elemental Analyses

| | | Calculated | | | Found | | |
|---|---|---|---|---|---|---|---|
| Compound | Formula | % C | % H | % N | % C | % H | % N |
| 10a | $C_{12}H_{18}N_4O_2S$ | 51.10 | 6.42 | 19.84 | 51.15 | 6.48 | 19.89 |
| 10b | $C_{16}H_{26}N_4O_2S.H_2O$ | 53.92 | 7.90 | 15.71 | 53.96 | 7.80 | 15.93 |
| 10c | $C_{11}H_{12}N_4O_3S$ | 47.14 | 4.32 | 20.00 | 47.15 | 4.20 | 19.82 |
| 10d | $C_{11}H_{12}N_4O_3S$ | 47.14 | 4.32 | 20.00 | 47.16 | 4.26 | 19.91 |
| 10e | $C_{15}H_{20}N_4O_3S$ | 53.56 | 5.99 | 16.65 | 53.60 | 6.10 | 16.46 |
| 10f | $C_{15}H_{20}N_4O_3S$ | 53.56 | 5.99 | 16.65 | 52.95 | 6.06 | 16.43 |
| 10g | $C_{11}H_{12}N_4O_2S_2$ | 44.58 | 4.08 | 18.90 | 44.43 | 4.24 | 18.86 |
| 10h | $C_{15}H_{20}N_4O_2S_2$ | 51.13 | 5.72 | 15.90 | 50.92 | 5.59 | 15.75 |
| 13 | $C_{12}H_{16}N_4OS$ | 54.52 | 6.10 | 21.20 | 54.44 | 6.35 | 21.25 |
| 14 | $C_{16}H_{24}N_4OS$ | 59.99 | 7.55 | 17.50 | 59.97 | 7.68 | 17.58 |
| 17 | $C_{11}H_{10}N_4O_2S$ | 50.40 | 3.84 | 21.36 | 50.43 | 3.79 | 21.32 |
| 18 | $C_{11}H_{10}N_4O_2S$ | 50.40 | 3.84 | 21.36 | 50.29 | 3.88 | 21.30 |
| 19 | $C_{15}H_{18}N_4O_2S$ | 56.60 | 5.69 | 17.60 | 56.14 | 5.66 | 17.25 |
| 20 | $C_{15}H_{18}N_4O_2S$ | 56.60 | 5.69 | 17.60 | 56.10 | 5.69 | 17.27 |
| 21 | $C_{11}H_{10}N_4O_2S_2$ | 47.46 | 3.62 | 20.13 | 47.72 | 3.62 | 20.09 |
| 22 | $C_{15}H_{18}N_4OS_2$ | 53.88 | 5.43 | 16.74 | 53.75 | 5.50 | 16.68 |
| 26 | $C_{13}H_{12}N_4OS$ | 57.34 | 4.44 | 20.54 | 57.62 | 4.46 | 20.51 |
| 33 | $C_{22}H_{30}N_6O_3S.1/4H_2O$ | 57.06 | 6.64 | 18.15 | 56.92 | 6.61 | 18.06 |
| 35 | $C_{23}H_{32}N_6O_3S.3/4H_2O$ | 56.83 | 6.95 | 17.29 | 56.81 | 6.62 | 17.19 |
| 37 | $C_{24}H_{34}N_6O_3S.1/2H_2O$ | 58.16 | 7.12 | 16.96 | 57.94 | 6.91 | 16.86 |
| 39 | $C_{40}H_{54}N_8O_8S$ | 59.54 | 6.75 | 13.89 | 59.51 | 6.76 | 13.82 |
| 41 | $C_{37}H_{47}F_3N_8O_8S.1/2CF_3COOH.1/2H_2O$ | 51.46 | 5.51 | 12.63 | 51.31 | 5.48 | 12.50 |
| 43 | $C_{27}H_{40}N_8O_4S.3HBr.3/2H_2O$ | 38.49 | 5.50 | 13.30 | 38.06 | 5.35 | 12.93 |
| 45 | $C_{33}H_{43}N_7O_8S$ | 56.80 | 6.21 | 14.05 | 56.95 | 6.54 | 15.42 |
| 46 | $C_{27}H_{32}N_6O_5S.H_2O$ | 56.83 | 6.01 | 14.73 | 56.98 | 5.76 | 14.84 |
| 48 | $C_{27}H_{31}N_6O_5SI.2.5H_2O$ | 44.82 | 11.61 | 44.60 | 4.54 | 11.48 | |
| 52 | $C_{12}H_{16}N_4S_2$ | 51.40 | 5.75 | 19.99 | 51.60 | 5.83 | 19.64 |
| 53 | $C_{16}H_{24}N_4S_2$ | 57.14 | 7.20 | 16.65 | 57.27 | 7.15 | 16.62 |
| 54 | $C_{12}H_{16}N_4OS$ | 54.52 | 6.10 | 21.20 | 54.52 | 6.17 | 21.18 |
| 55 | $C_{10}H_{24}N_4OS$ | 59.99 | 7.55 | 17.50 | 59.89 | 7.56 | 17.35 |
| 56 | $C_{13}H_{12}N_4OS$ | 57.33 | 4.44 | 20.58 | 57.44 | 4.48 | 20.52 |
| 57 | $C_{15}H_{16}N_4OS$ | 59.32 | 5.97 | 18.65 | 58.52 | 5.59 | 18.12 |
| 60b | $C_{11}H_9NO_3SHg$ | 26.25 | 2.20 | 3.40 | 26.20 | 2.19 | 3.46 |
| 61a | $C_6H_5O_2SI.0.5H_2O$ | 26.01 | 2.18 | — | 25.74 | 2.03 | — |

What is claimed is:

1. A pharmaceutical composition comprising a compound of the formula:

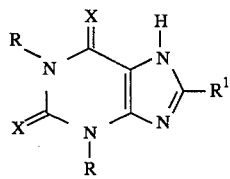

wherein X is O or S, with the proviso that at least one X is S; R is an alkyl of 1–12 carbons which may be substituted with an hydroxy, amino or halo group; and $R^1$ is a furyl or thienyl group, or a phenyl group substituted with a substituent $R^2$ which is a member selected from the group consisting of —$CONH(CH_2)_nNHR^3$ where n=2–10, alkyoxyamide, benzyloxyamide, and alkylamino, and $R^3$ is alkyl, alkylcarbonyl, or alkoxyamidoalkyl, and a pharmaceutically acceptable carrier.

2. The composition of claim 1 which is an elixir.

3. The composition of claim 1 which is in tablet form.

4. The composition of claim 1 adapted for administration through the mucosa.

5. The composition of claim 4 which is adapted for inhalation.

6. A pharmaceutical composition comprising a compound of the formula:

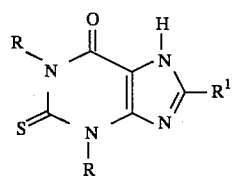

wherein R is an alkyl of 1–12 carbons which may be substituted with an hydroxy, amino or halo group; and $R^1$ is a cycloalkyl, and a pharmaceutically acceptable carrier.

7. The composition of claim 6, wherein $R^1$ is cyclopentyl.

8. The composition of claim 7, wherein said compound is 1,3-dipropyl-8-cyclopentyl-2-thioxanthine.

9. The composition of claim 7, wherein said compound is 1,3-dimethyl-8-cyclopentyl-2-thioxanthine.

10. A compound of the formula:

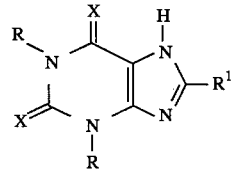

wherein X is O or S, with the proviso that at least one X is S; R an alkyl of 1–12 carbons which may be substituted with an hydroxy, amino or halo group; and $R^1$ is a furyl or thienyl group, or a phenyl group substituted with a substituent $R^2$ which is a member selected from the group consisting of —$CONH(CH_2)_nNHR^3$ where n=2–10, alkoxyamide, benzyloxyamide, and alkylamino, and $R^3$ is alkyl, alkylcarbonyl, or alkoxyamidoalkyl.

11. The composition of claim 1, wherein said compound is 1,3-dimethyl-8-(2-thienyl)-2-thioxanthine.

12. The composition of claim 1, wherein said X at the 2-position is S.

13. The composition of claim 12, wherein
$R^1$ is a phenyl group substituted with a substituent $R^2$ which is a member selected from the group consisting of alkoxyamide, benzyloxyamide, alkoxyamidoalkyl, and —$CONH(CH_2)_nNHR^3$ where n=2–10, and $R^3$ is alkyl, alkylcarbonyl, or alkoxyamidoalkyl.

14. The composition of claim 1, wherein said compound is 1,3-dipropyl-8-(2-thienyl)-2-thioxanthine.

15. The composition of claim 10, wherein $R^1$ is furyl.

16. The composition of claim 10 wherein $R^1$ is thienyl.

17. The compound of claim 10, wherein said X at the 2-position is S.

18. The compound of claim 17, wherein $R^1$ is furyl.

19. The compound of claim 17, wherein $R^1$ is thienyl.

20. The compound of claim 17, wherein $R^1$ is a phenyl group substituted with a substituent $R^2$ which is a member selected from the group consisting of —$CONH(CH_2)_nNHR^3$ where n=2–10, alkoxyamide, benzyloxyamide and alkylamino, and $R^3$ is alkyl, alkylcarbonyl, or alkoxyamidoalkyl.

21. A compound of the formula:

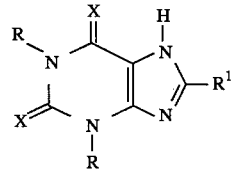

wherein R is an alkyl of 1–12 carbons which may be substituted with an hydroxy, amino or halo group; and $R^1$ is a cycloalkyl.

22. The compound of claim 21, wherein $R^1$ is cyclopentyl.

23. The compound of claim 22, wherein said compound is 1,3-dipropyl-8-cyclopentyl-2-thioxanthine.

24. The composition of claim 22, wherein said compound is 1,3-dimethyl-8-cyclopentyl-2-thioxanthine.

25. The compound of claim 10, wherein said compound is 1,3-dimethyl-8-(2-thienyl)-2-thioxanthine.

26. The compound of claim 10, wherein said compound is 1,3-dipropyl-8-(2-thienyl)-2-thioxanthine.

* * * * *